US012797612B2

(12) United States Patent
Pretzer-Aboff et al.

(10) Patent No.: US 12,797,612 B2
(45) Date of Patent: Nov. 17, 2026

(54) GAIT AND BALANCE ASSISTIVE STIMULATION DEVICE

(71) Applicant: VIRGINIA COMMONWEALTH UNIVERSITY, Richmond, VA (US)

(72) Inventors: Ingrid Pretzer-Aboff, Richmond, VA (US); Eva Stwodah, Richmond, VA (US); Alice Babashak, Richmond, VA (US); Noah Helm, Richmond, VA (US); Patricia Brown, Richmond, VA (US); Yasmeen Baig, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 532 days.

(21) Appl. No.: 18/002,074

(22) PCT Filed: Jun. 16, 2021

(86) PCT No.: PCT/US2021/037567

§ 371 (c)(1),
(2) Date: Dec. 16, 2022

(87) PCT Pub. No.: WO2021/257661

PCT Pub. Date: Dec. 23, 2021

(65) Prior Publication Data

US 2023/0226350 A1 Jul. 20, 2023

Related U.S. Application Data

(60) Provisional application No. 63/039,720, filed on Jun. 16, 2020.

(51) Int. Cl.
*A61N 1/36* (2006.01)
*A61H 23/02* (2006.01)
*A61N 1/04* (2006.01)

(52) U.S. Cl.
CPC ......... *A61N 1/36003* (2013.01); *A61H 23/02* (2013.01); *A61N 1/0484* (2013.01); *A61N 1/0488* (2013.01)

(58) Field of Classification Search
CPC .............. A61N 1/36003; A61N 1/0484; A61N 1/0452; A61H 2201/164
See application file for complete search history.

(56) References Cited

U.S. PATENT DOCUMENTS

| | | | |
|---|---|---|---|
| 5,913,838 | A | 6/1999 | Reilly |
| 6,453,204 | B1 | 9/2002 | Rhodes |
| 8,692,675 | B2 | 4/2014 | Agrawal et al. |
| 2006/0085047 | A1 | 4/2006 | Unsworth et al. |
| 2007/0255187 | A1 | 11/2007 | Branch et al. |
| 2010/0249637 | A1 | 9/2010 | Walter et al. |
| 2011/0232134 | A1 | 9/2011 | Radt et al. |
| 2022/0015500 | A1 | 1/2022 | Pretzer-Aboff et al. |

*Primary Examiner* — Joseph M Dietrich
(74) *Attorney, Agent, or Firm* — WCF IP

(57) ABSTRACT

Provided are stimulation devices for improving ambulatory activity of a subject in need thereof. The device includes a foot covering for holding two battery-operated tactile actuators on a metatarsal region and an ankle region of the wearer's foot. The foot covering also includes a detachable material for housing and securing the two tactile actuators and a pouch region for holding electronics.

20 Claims, 10 Drawing Sheets

GAIT AND BALANCE ASSISTIVE STIMULATION DEVICE

CROSS REFERENCE TO RELATED APPLICATIONS

This application claims priority to and benefit of U.S. Provisional Patent Application No. 63/039,720, filed on Jun. 16, 2020, which is hereby incorporated by reference herein in its entirety.

FIELD OF THE INVENTION

The disclosure relates to a wearable stimulation device for providing vibration and/or neuro-stimulation for a subject in need thereof. In particular, the device is a two-part foot stimulation device having a wearable foot covering and a detachable material for holding two battery-operated tactile actuators. The detachable material is configured to be securely affixed on the outer surface of the foot covering for providing vibratory stimulation at the metatarsal region and the lateral plantar region when the stimulation device is worn by the wearer. The device may further include at least one electronic controller, a pouch region for holding electronics, and a passageway for any wires used for connecting the electronics to the tactile actuators.

BACKGROUND

Parkinson's disease (PD) is caused by a dopamine deficiency in the basal ganglia that results in characteristic motor abnormalities including postural instability and gait impairment. Nearly 60 percent of people with Parkinson's disease experience the sudden inability to walk, a phenomenon referred to as "freezing of gait." It manifests in a complete stop or prolonged shuffle despite the individual's best intentions to move forward and can be triggered mid-stride by a cluttered mom, narrow spaces like a doorway or when making a turn. Although PD is primarily a motor disease, accumulating evidence suggest that progressive degeneration of the central nervous system and/or abnormal proprioception and kinesthesia contribute to the parkinsonian gait. PD patients have reduced sensation on the plantar feet and impaired joint position sense, movement perception, and movement accuracy. No medications or surgeries currently are available to effectively treat the symptoms.

To reduce the motor sensory symptoms, a mechanical stimulation of foot mechanoreceptors upon static balance as a mean for proprioceptive feedback modulation has been suggested to improve the quiet-standing balance in healthy controls and in patients with conditions that are implicated with peripheral somatosensory function problems diabetes, stroke, PD, aging, neuropathy, etc.). In general, specialized mechanoreceptor neurons transduce mechanical stimuli from the body's interaction with the environment into electrical signals that can be transmitted and interpreted by the nervous system. Sensory cells of all types are typically threshold-based units. That is, if the stimulus to a sensory cell is of insufficient magnitude, the cell will not activate and begin signaling. Such a stimulus is called subthreshold while a stimulus which is above the threshold is called suprathreshold. The use of subthreshold stimulation to enhance the function of sensory cells is described in U.S. Pat. Nos. 5,782,873 and 6,032,074 to Collins and U.S. Pat. Application 2017/0165486 to Harry.

Vibration therapy has also been found effective for reducing some of the motor sensory symptoms experienced by PD patients. The vibration therapy has its roots with 19$^{th}$ century French neurologist Jean-Martin Charcot, who used vibration therapy as a treatment for PD. A vibration chair for PD patients was developed based on the observation of the PD patients experiencing improved movement after a train or carriage ride. While many PD patients report some improvements in their abilities to move with current physical rehabilitation therapy, full recovery from PD or stroke and regaining motor sensory function is uncommon, thus other continuous boosting or assisting measures are often necessary. An exemplary assistive method is to provide a vibration stimulation of foot mechanoreceptors, which has been shown to improve gait. Other stimulations or cueing such as visual and vibration have been shown to improve the gait and reduce tremor and rigidity of PD's patients. However, such assistive methods require complicated devices with limited availability provided in only certain environments (e.g., hospitals, clinics, rehabilitation centers, etc.). Further, it has been found that adjusting the system for individual needs or providing a sufficient effect of the vibration or stimulation is complex, due to various controlling factors frequency, amplitude and location of the vibration stimulation).

Thus, there is a need in the art for an improved wearable device providing an effective assistive vibration or electric stimulation that is cost-effective, lightweight, non-invasive, easy to use and adjustable to variety of therapeutic applications, e.g., in PD or in stroke patient therapy.

SUMMARY OF THE INVENTION

The present disclosure relates to a foot stimulation device, particularly a two-part wearable stimulation device having at least one foot covering for use on a subject's foot and at least one detachable material for holding at least one tactile actuator, and in particular embodiments two tactile actuators, that are wired to a portable power source. The device is designed to assist and/or improve at least one of the motor sensory symptoms of Parkinson's disease (PD), neuropathy, diabetes, stroke or any other disorders or conditions that affect lower body movement such as walking or running. One of the main advantageous features of the present invention is that the subject can easily wear the device by putting on the foot covering portion of the device, which already has built-in vibratory stimulators (i.e., tactile actuators). The locations of the tactile actuators on the foot covering may be determined based on the analysis of individual subject or a general PD research. The prearrangement of the tactile actuators on a wearable foot covering eliminates the difficulty often observed in PD patients, which is to apply the electric components for vibratory stimulation after wearing any footwear on their foot. The device may also be designed based on human factors research to ensure its comfort, ease of use and many other convenient features such as being washable and visually pleasing. The device may also be worn with a shoe or additional devices.

One aspect of the disclosure provides a stimulatory device configured for operation with tactile actuators which stimulate the metatarsal and plantar regions of a human foot. The device comprises a foot covering portion for use on a human foot having at least a foot top region, an ankle region and an electronics-holding pouch region. In preferred embodiments, the foot top region may be aligned with a metatarsal region of the subject's foot when the foot covering is placed on the subject's foot whereas the ankle region may be aligned with at least one side of an ankle of the subject's foot when the foot cover is placed on the subject's foot. The pouch region is designed to be placed away from the foot top region and the ankle region on the foot covering. The device further comprises a detachable and securable material to be placed on the foot covering. The detachable material has a first placement region for a first tactile actuator in the foot top region of the foot covering and a second placement region for a second tactile actuator in the ankle region of the foot covering. In the cases where the electronics are wired to the two tactile actuators, a passageway on the detachable material may be created for wires to extend from the electronics holding pouch region to the first placement and the second placement regions housing the two tactile actuators. In some embodiments, the detachable and securable material may be attached or secured to the foot covering by hook-and-loop fasteners. In some embodiments, the detachable material is secured to the foot covering by an adhesive.

In preferred embodiments, the electronic holding pouch may be strapped around the subject's ankle while in use. The device may further include an electronic controller for adjusting the magnitude of vibration and/or a sensor for detecting the pressure input during an ambulatory activity of the user. In some embodiments, the foot covering is configured as a plurality of types of socks such as a crew sock, an ankle sock, a toeless sock and a cuff.

Another aspect of the disclosure provides a stimulation device which comprises a foot covering for use on a subject's foot having at least a foot top region, an ankle region, and an electronics holding pouch region, wherein the foot top region is alignable with a metatarsal region of the human foot when the foot covering is placed on the human foot, wherein the ankle region is alignable with at least one side of an ankle of the human foot when the foot cover is placed on the human foot, and wherein the pouch region is spaced away from the foot top region and the ankle region on the foot covering; a first tactile actuator; a second tactile actuator; an electronic controller; wires which connect the electronic controller to the first tactile actuator and the second tactile actuator; and a material detachable from and securable to the foot covering, wherein the material creates a first placement region for the first tactile actuator in said foot top region of the foot covering and permits the first tactile actuator to provide vibratory stimulation to the metatarsal region of the human foot, wherein the material creates a second placement region for a second tactile actuator in said ankle region of the foot covering and permits the second tactile actuator to provide vibratory stimulation to a plantar region of the human foot, and wherein the material creates a passageway for the wires to extend from the electronics holding pouch region to the first placement region and the second placement region. The passageway may be designed to sufficiently contain the wires from becoming a tripping hazard when the device is worn in the community setting. The detachable and securable material may be attached or fastened to the foot covering by hook-and-loop connectors. In other embodiments, the detachable material is secured to the foot covering by an adhesive.

In some embodiments, the stimulation device further comprises a battery connected to the electronic controller, wherein the pouch region holds both the electronic controller and the battery. In preferred embodiments, the electronic holding pouch may be strapped around the subject's ankle when the stimulation device is worn by the wearer. The device may further include a controller for adjusting the magnitude of vibration and a sensor for detecting the pressure input during an ambulatory activity of the user. In some embodiments, the foot covering is configured as a plurality of types of socks such as a crew sock, an ankle sock, a toeless sock and a foot cuff.

Additional features and advantages of the present invention will be set forth in the description of disclosure that follows, and in part will be apparent from the description of may be learned by practice of the disclosure. The disclosure will be realized and attained by the compositions and methods particularly pointed out in the written description and claims hereof.

DETAILED DESCRIPTION

The preferred embodiments of the present disclosure are directed toward stimulation devices for assisting and/or improving ambulatory activities (e.g., gait and balancing) of a subject in need thereof. The stimulation device may be used while a subject ambulates on a treadmill or during normal point-to-point ambulation as well as balancing during any types of movements. The stimulation devices disclosed herein are particularly suitable for users with degenerative neurological disorders including Parkinson's disease, neuropathy, multiple sclerosis, cerebral palsy, ataxia and stroke. Other exemplary disorders or conditions that may also benefit from using the stimulation device of the present invention include foot pain, poor circulation, diabetes, aging or any other conditions that affect walking or running and those of which would benefit from a vibration therapy or vibration feedback described in U.S. Pat. No. 8,692,675, incorporated herein by reference.

The term, "movement" or "locomotion" or "ambulatory activity", as used herein, refers to any movements involving two or more interrelated functions, such as i) track, which may include a walking, running or other dynamic activity from forward footpath creation over firm surfaces such as the ground, water-floats, or snow and ice; and ii) balance, which describes a state being required to efficiently move the lower body and/or upper body under track.

The stimulation device disclosed herein comprises at least one layer of material to form a foot covering for receiving a portion of foot, ankle and/or calf of the subject, at least one outer attachment affixed to at least a portion of the foot covering, at least one and preferably two tactile actuators for providing vibratory stimulation and at least one battery to power the two tactile actuators. The term, "foot covering", as used herein, is not intended to refer to any particular category or style of footwear but rather intended to encompass any and all structures adapted to be secured to a wearer's foot. The foot covering may include a sock or shoe which may be fully covering the entire portion of the foot up to the top of the ankle. Alternatively, in some embodiments, the foot covering may be a toeless sock or shoe such as a foot cuff, a foot wrap, a sandal, an athletic shoe, a running shoe, a boot, a slipper or a flip-flop. In preferred embodiment of this disclosure, the foot covering is a sock. The sock may be a crew sock, an ankle sock, a cuff or a toeless sock.

Figure 1:
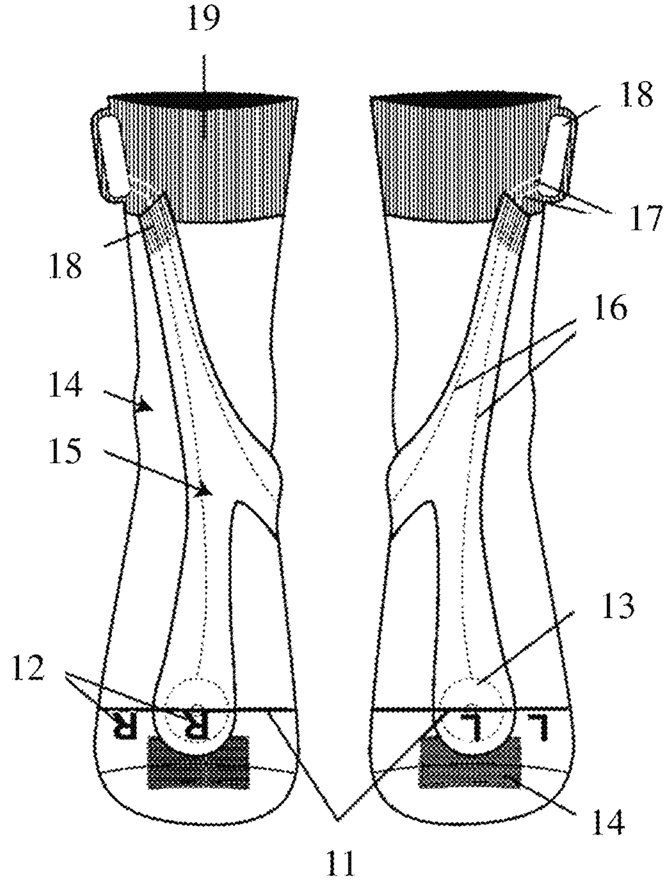
FIG. 1 illustrates a front view a stimulation device having a foot covering portion and a detachable material portion according to the present invention.

Referring to FIG. 1, an exemplary stimulation device is a two-part sock 11 configured to fit either a right foot or a left foot of a human subject with various types of indicative markings 12 (e.g., raised contrast by knitting R for a right foot and L for a left foot). The two-part stimulation device comprises a foot covering sock portion 14 and a detachable and securable material portion 15 for use on a subject's foot. The foot covering portion has a foot top region that may be aligned with a metatarsal region of the foot 13 when the foot covering is worn by the wearer. The foot covering also has an ankle region which may be aligned with at least one side of an ankle of the wearer. In preferred embodiments, the foot covering also includes a pouch region 18 for holding electronics (e.g., battery, controllers, etc.). The detachable and securable material portion 15, having two placement regions for tactile actuators, is configured to be attached to multiple portions of the foot covering as shown in FIG. 1. At least two tactile actuators are placed inside the detachable material 15 which covers a metatarsal region 13 and a lateral plantar region of the foot. In some embodiments, one tactile actuator is placed in a first placement region of the detachable material in the foot top region 13 of the foot covering and another tactile actuator is housed in a second placement region of the detachable material in the ankle region of the foot covering. In some embodiments, the tactile actuators are connected to electronics by wires. In other embodiments, the tactile actuators are wirelessly connected to the electronics. When the tactile actuators are wired to the electronics, the connecting wires may be securely contained or secured in a passageway 16 created in the inner portion of the detachable material, having an optional elastic rib band at the opening of the passageway for tightly fastening at least one or more wires to the foot covering portion of the device. Further, the detachable material 15 may include a pouch for holding electronics so that the wires 17 connected to the electronics in the pouch may extend to the first placement region and the second placement region holding tactile actuators. The pouch may be located on the outer side of the calf just above the distal end of the fibula or lateral malleolus, which is the bony protrusion on the outside of the ankle.

The foot covering portion of the sock may be made of at least one layer of one or more materials. The materials used for the part may be any flexible or elastic materials in order to accommodate various foot sizes. In preferred embodiments, the layer of material is desirably comprised of thin, non-cushioned materials, such as a cotton or polyester, in order to improve conduction of vibratory stimulation to the user's foot. Alternatively, two, three or more layers of sock materials may be used to manufacture the foot covering portion of the device, in some embodiments, a thick multi-layered material may be desirable to maintain a fixed, molded form of the device. Other suitable structures or materials for use as a foot covering will be known to one of ordinary skill in the art from the description herein. Exemplary materials which can be used in the practice of the invention include but are not limited to: cotton, rayon, flax, Modal, polyester, wool, silk, viscose rayon, nylon, acrylic, spandex, olefin, microfibers, lyocell, angora, alpaca or combinations thereof. Both the foot covering portion and the detachable material portion may also comprise materials having moisture wicking property. Further, some portions of the sock may include additional material 19 (e.g., rib welt band) that extends around the ankle of the wearer to prevent the foot covering from sliding down or slipping off from the foot.

In preferred embodiments, the foot stimulation device comprises at least one of outer attachment which covers to various areas of the foot, ankle and/or calf of the wearer. These outer detachable materials are configured to house one or more tactile actuators. The term, "tactor" or "tactile actuator", as used herein, refers to a small actuator that vibrates against the skin to provide a physical stimulus in response to an electrical input. Various shapes, sizes, peak frequencies, weights of the tactile actuators may be contemplated for the stimulation device disclosed herein. Desirably, vibration tactile actuators may provide a vibration frequency in the range of approximately 100-450 Hz, preferably 150-400 Hz, more preferably 200-350 Hz. In another embodiments, the tactile actuators may provide a frequency in the range of approximately 1-80 Hz, preferably 2-60 Hz, more preferably 3-40 Hz. Each of the plurality of tactile actuators may provide a particular vibration having a controllable amplitude and frequency. For example, the amplitude or frequency of the tactile actuators may be selected separately and independently from one another. Different tactile actuators are to be wired in series to distribute the voltage between the two or more tactile actuators and prevent those from warming up.

Figures 2A, 2B, 2C:
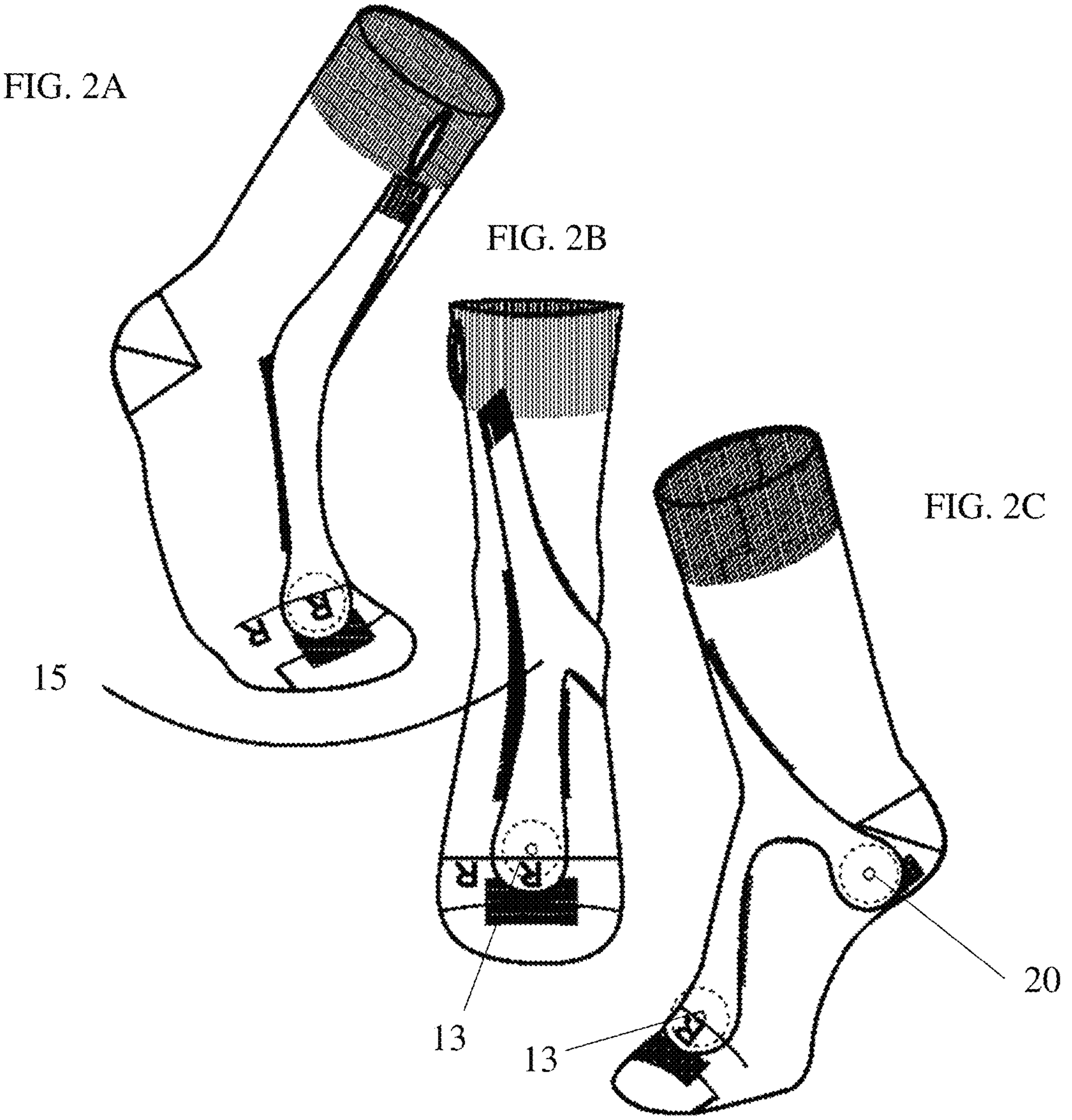
FIGS. 2A-C illustrate a (A) right side view, (B) front view and (C) left side view of an exemplary embodiment of the stimulation device with the detachable material holding two tactile actuators affixed on the surface of the foot covering.

Referring to FIGS. 2A-C, in some embodiments, the outer detachable material 15 comprises two prongs (i.e., two placement regions for tactile actuators) that are placed to be aligned with a metatarsal region and at least one side of an ankle of the wearer's foot. In some embodiments the detachable material is made up by two different layers including the upper layer constructed from the same material as the layer of sock materials (e.g., jersey sock textile) and the under layer constructed from a lighter weight jersey material. The outer detachable material may be attached to the foot covering layer at the metatarsal 13 and lateral plantar 20 of the wearer.

Figure 3A:
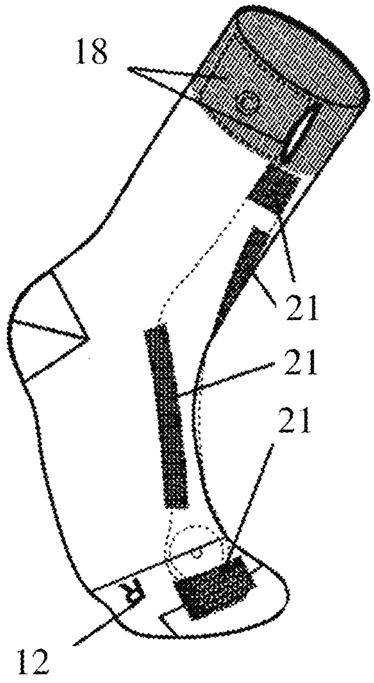
FIGS. 3A-D illustrate an exemplary embodiment of the device of FIGS. 2A-C, showing a (A) right side view, (B) front view and (C) left side view of the foot covering portion and (D) the detachable material portion with a hook-and-loop fastening system.
Figure 3B:
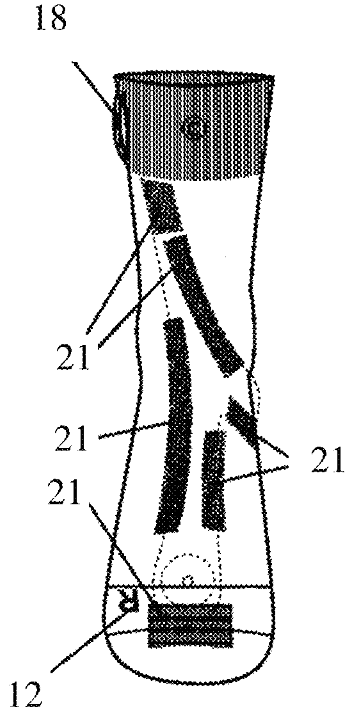
Figure 3C:
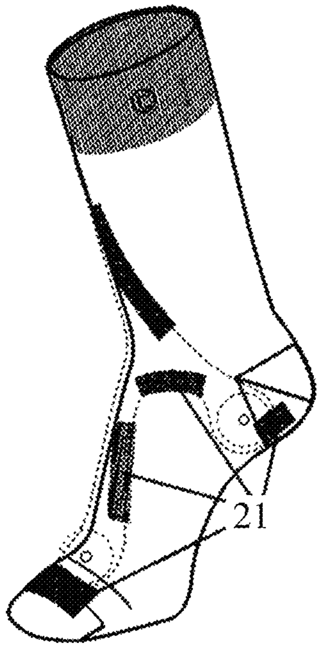
Figure 3D:
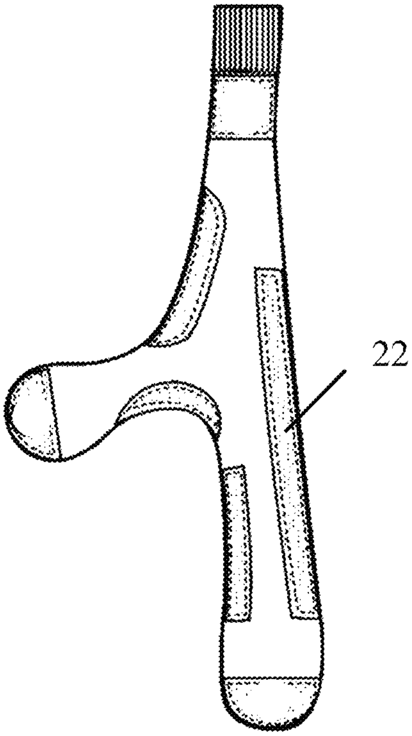

Referring to FIGS. 3A-D, to securely place the tactile actuators on the outer surface of the foot covering, various means of attachment may be used. In some embodiments, adhesives, such as a medical grade double sided adhesive, medical tape, elastic strap, strap with snaps, hook-and-loop (e.g., Velcro) fasteners or other fasteners, may be employed to secure the outer detachable material onto the foot covering surface. In preferred embodiments, a hook-and-loop fastener is employed on some portions of the foot covering 21 and the under layer of the outer detachable material. The hook-and-loop fastener generally consists of two components, typically, two linear fabric strips which are attached to the opposing surfaces to be fastened. In some embodiments, the first component featuring layers of small loops are attached on the surface 21 of the foot covering (FIGS. 3A-C) while the second component featuring layers of small hooks are attached on the foot covering-facing surface 22 of the detachable material (FIG. 3D). As shown in FIG. 3D, the detachable material may be in a triangular star shape having at least two fingers with different lengths stemmed from the opening region of the foot covering, for example, one finger configured to extend up to the wearer's metatarsal region while another finger is configured to be positioned at one side of the lateral plantar when the stimulation device is worn by the wearer. In some embodiments, other shapes having more than two fingers (e.g., three, four, five, six arms or more) may also be contemplated for some embodiments of the present invention, in which the shapes of the foot covering and/or the detachable material may be based on the curved shape and/or angle of the foot and ankle regions.

Figure 4A:
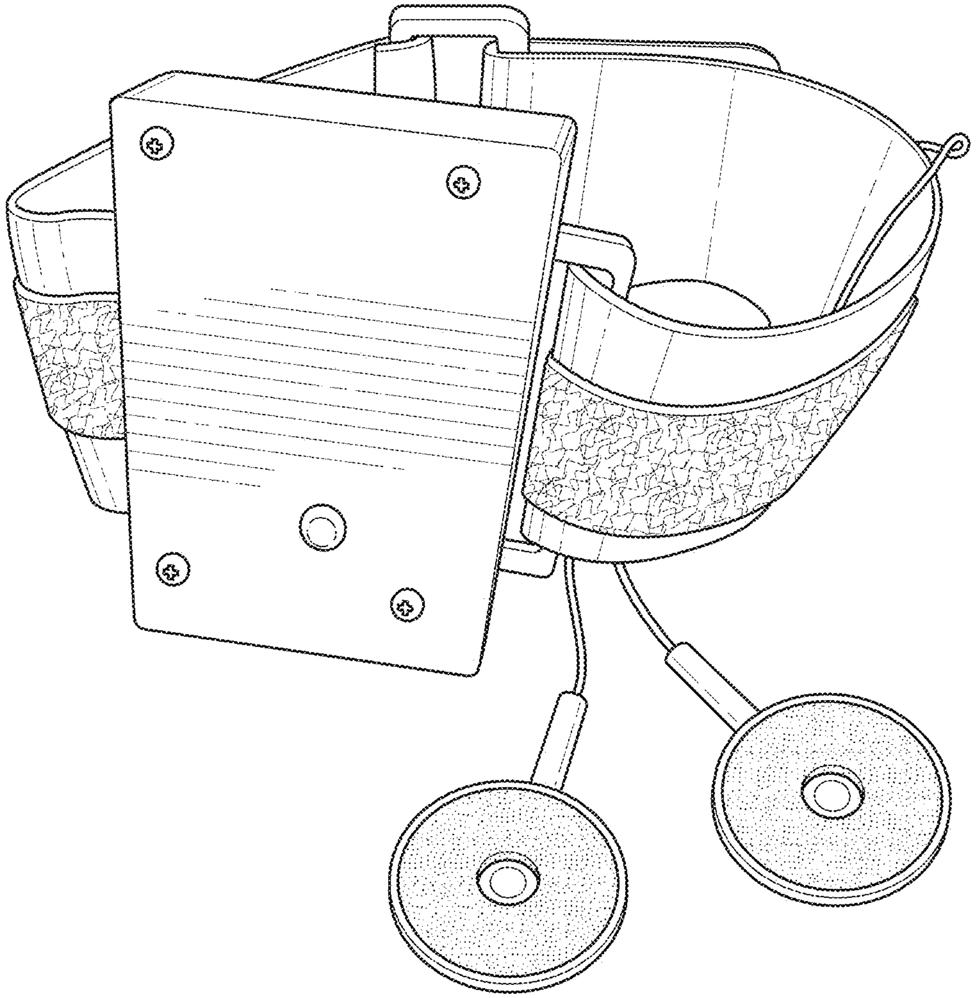
FIGS. 4A-B show (A) an exemplary battery and two tactile actuators with an ankle strap and (B) an exemplary configuration and position of the stimulation device of the present invention when worn with a shoe.
Figure 4B:

Referring to FIGS. 4A-B, the stimulation device comprises a portable power source, in this case, a portable battery. The power source may include an embedded processor and a controller, which may be connected to each other by wires. The power supply is selected based on the required voltage and current for operating the processors, controllers, sensors as well as the tactile actuators. Some exemplary power source includes a lightweight rechargeable lithium ion battery pack, disposable non-researchable batteries or any other lightweight portable power supply. In some embodiments, the battery may have a nominal voltage of 3.6 VDC with a minimum capacity of 1600 mAh and about 3 hours of run time between charges. Alternatively, a rechargeable battery with 4.2 VDC and a charge time about 4 hours may be used. The stimulation device may further include at least one electronic controller or at least one sensor for turning on or off the device, adjusting the magnitude of vibration and/or detecting the pressure input during an ambulatory activity of the user. Additionally, in some embodiments, one or more sensors may be placed at the heel, ball and/or toe of the foot for measuring the phases of gait. For example, the force sensing variable resistors may be connected to a microprocessor in a voltage divider circuit; the voltage across the fixed resistor in the circuit which may be measured by the onboard 10-bit ADC built into the Arduino microprocessor. In some embodiments, the sensor, tactile actuator, controller, processor and/or power source of the footwear may be synchronized to each other, either wirelessly or by wiring. As shown in FIG. 4B, the power source may employ a controller, a portable battery and/or a processor to be connected and wired to the tactile actuators. The power source may further be attached with or without an ankle strap to be placed on the subject's ankle while in use. Alternatively, the power source may be shaped and sized to be small enough for conveniently placed in a electronic holding pouch to be worn around the ankle. Other electronics may also be included in the device and configured to be strapped around the ankle or any portion of the lower leg while securely placed in the pouch portion of the detachable material. As shown in FIG. 4B, the device can be worn with a shoe or any other additional devices.

Figure 5:
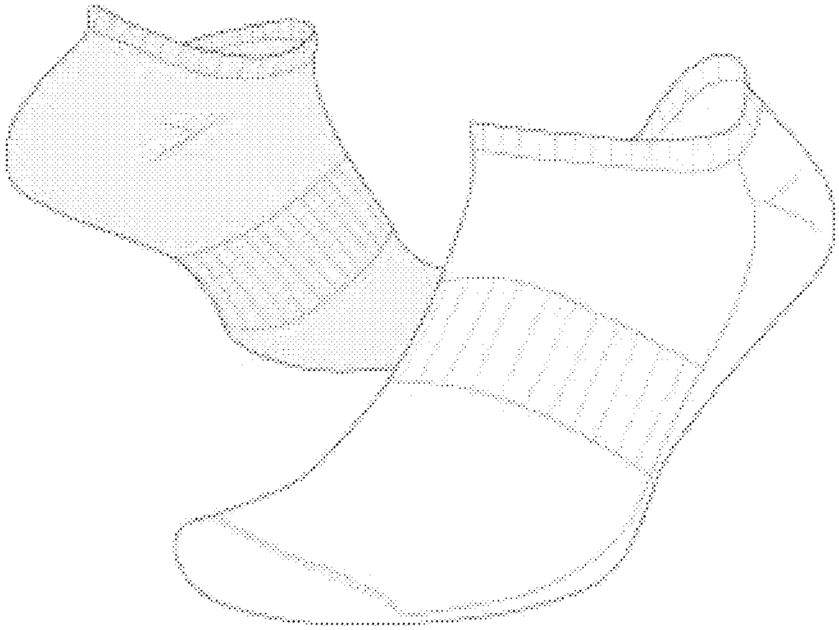
FIG. 5 is a schematic drawing of the foot covering configured as a crew sock.
Figure 6A:
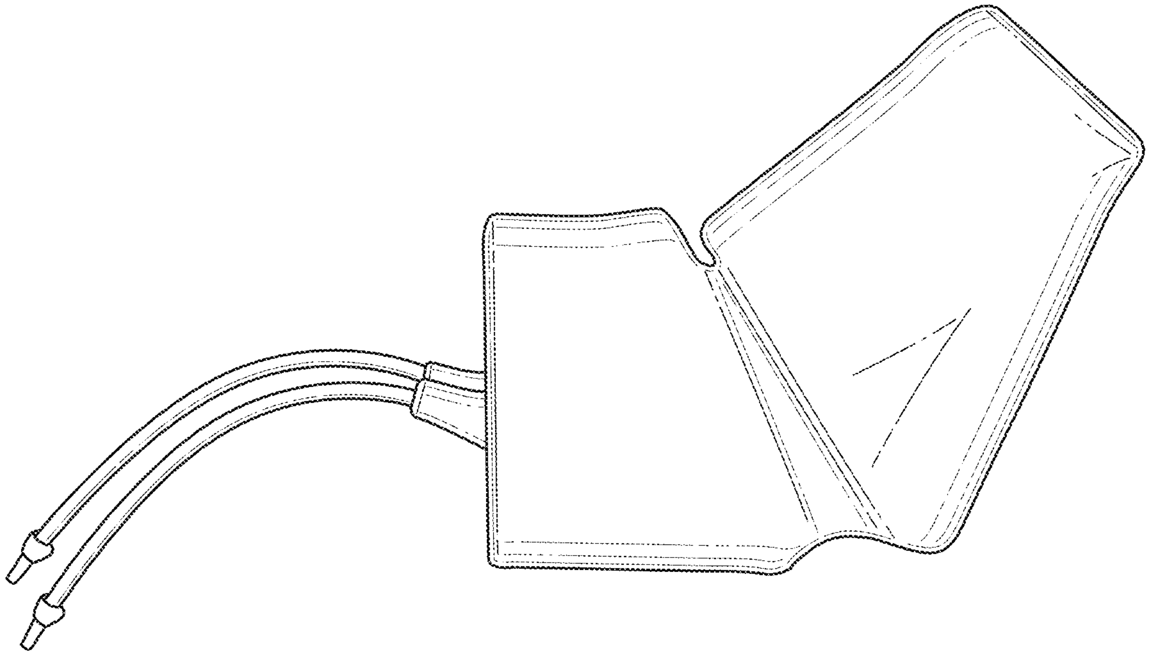
FIGS. 6A-C show (A) an exemplary foot covering configured as a cuff, (B) a demonstration of putting on the cuff through the opening and (C) a configuration and position of the cuff when worn by the wearer.
Figure 6B:
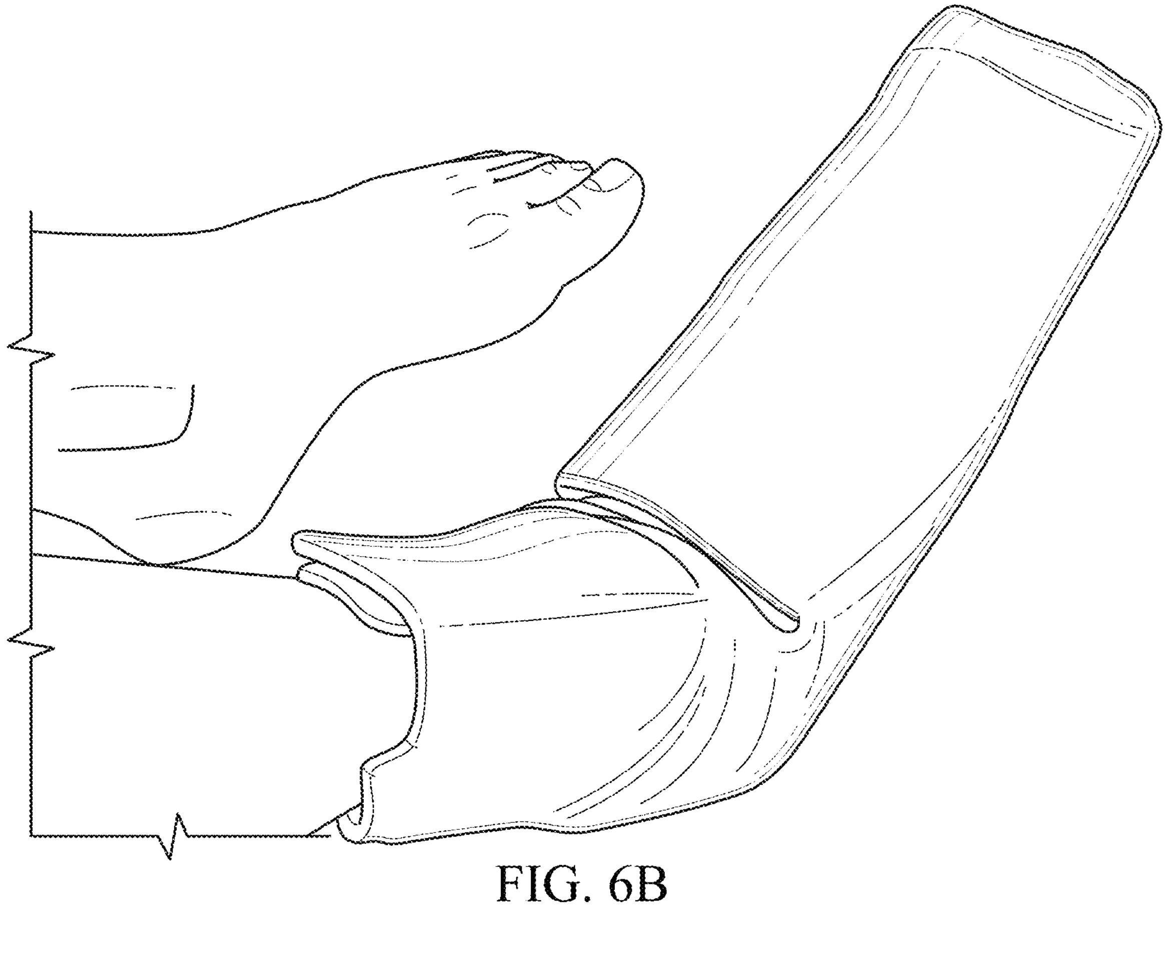
Figure 6C:
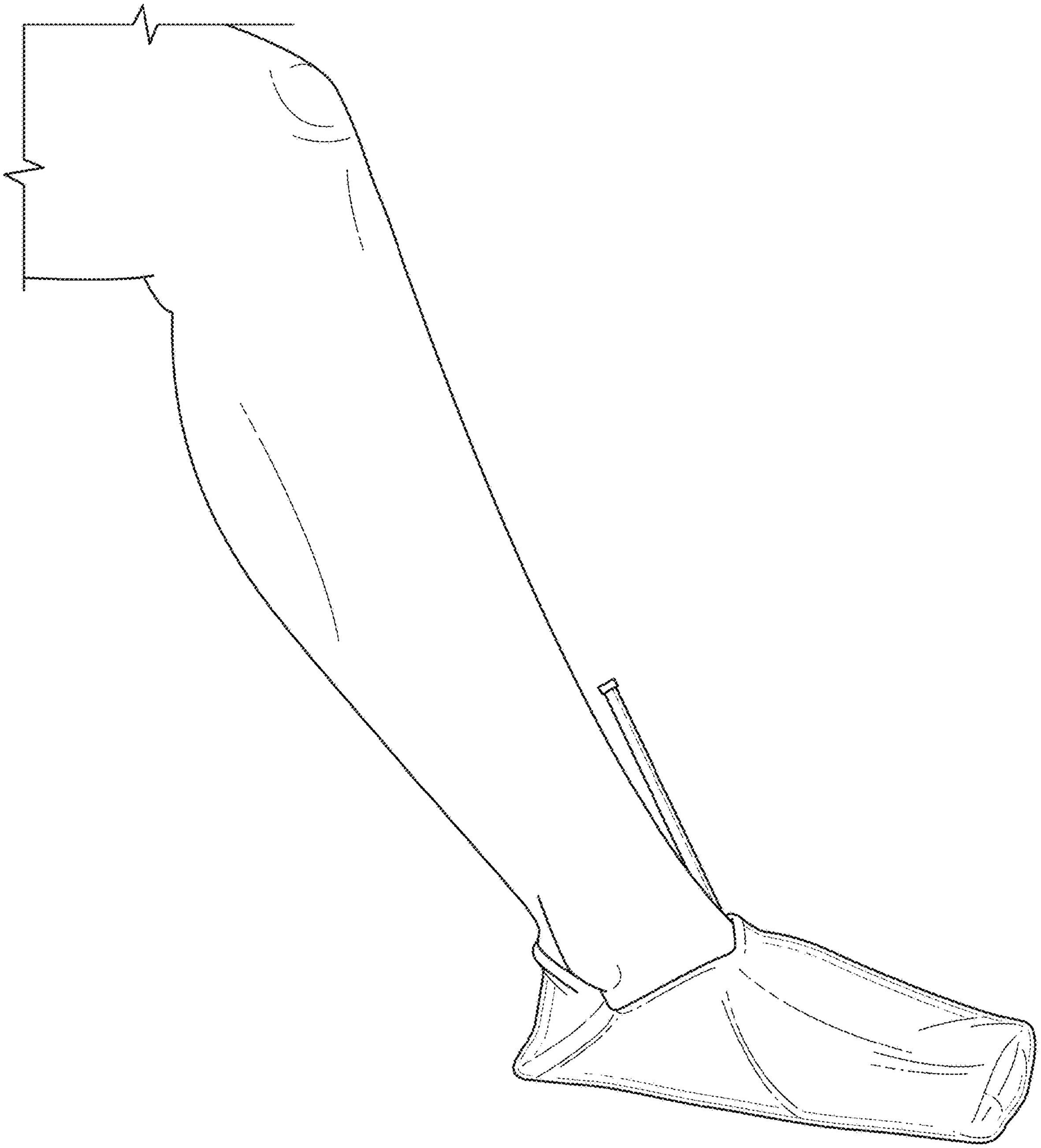
Figure 7:
FIG. 7 shows an exemplary foot covering configured as a toeless sock.

In some embodiments, the foot covering may be configured as an ankle sock as shown in FIG. 1. In some embodiments, the foot covering may be a crew sock or a low-cut sock as shown in FIG. 5. In other embodiments, the foot covering may be a cuff as shown in FIGS. 6A-C. In some embodiments, as shown in FIG. 7, the foot covering is a toeless sock. As described above, in some embodiments, the foot covering may be configured as any type of shoe or any other footwear including a sandal, a flip-flop or a boot. Other plurality of types of foot covering shapes may also be contemplated including a comfort fabric portion that may be similar to an athletic sock, calf-high sock, mid-calf sock, knee-high sock, slouch sock or the like that substantially covers the wearer's foot but also covers a portion of the wearer's leg.

In another embodiment, antibacterial or antimicrobial agents may be incorporated into the foot covering and/or detachable material of the stimulation device. Non-limiting examples of antimicrobials include gentamicin sulfate, penicillin, cephalothin, ampicillin, amoxicillin, augmentin, aztreonam, imipenem, streptomycin, gentamicin, vancomycin, clindamycin, erythromycin, azithromycin, polymyxin, bacitracin, amphotericin, nystatin, rifampicin, tetracycline, doxycycline, chloramphenicol, nalidixic acid, ciprofloxacin, sulfanilamide, gantrisin, trimethoprim, isoniazid, para-aminosalicylic acid, minocycline, hexachlorophene, cationic biguanides (i.e., chlorhexidine, cyclohexidine), iodine and iodophores (i.e., povidone-iodine), para-chloro-meta-xylenol, triclosan, furan medical preparations (i.e., nitrofurantoin, nitrofurazone), methenamine, aldehydes (glutaraldehyde, formaldehyde), silver sulfadiazine and alcohols, tetracyclines (e.g., minocycline), cephalosporins (e.g., cefazolin), other beta-lactam antibiotics (e.g., imipenem, aztreonam), and combinations thereof.

Example 1

Exemplary prototypes of movement assisting stimulation device are described here. The stimulatory device (i.e., PD Sock) of the present invention solves the problem of not having a wearable device that allows people diagnosed with Parkinson's disease to use the VibeForward (Resonate Forward LLC) in their home or community settings. The end users of our PD Sock product are the 800,000 people in the United States and over 8 million worldwide who suffer from disabling walking and balance issues resultant from Parkinson's disease. Patients progress at different rates but over 80% experience gait disorders including the most devastating symptom of Freezing of Gait (described as the inability to take a step forward, despite their will to do so). VibeForward is a non-invasive, breakthrough medical technology that reduces the symptoms of Freezing of Gait, shuffling and slowed walking to help patients regain their independence. Freezing of Gait is a symptom that is not been effectively treated by medications or deep brain stimulation, and for the patients that suffer from freezing the VibeForward could be their only option. The PD Sock is the only device that will allow for the VibeForward device to be used easily and safely in the home and community environment. The PD Sock works with the VibeForward technology so that it may be implemented by the PD population at large.

The PD Sock prototype coupled with the VibeForward technology is intended to allow the VibeForward device to be worn in the real-world settings, opening up the opportunity for improved gait, mobility and quality of life for people living with Parkinson's disease. To date, the VibeForward technology can only be used in the clinic or supervised research settings due to the exposed wires and clinical expertise necessary to place the electrical components properly on the user's feet. The PD Sock solves these problems.

Example 2

Figure 8A:
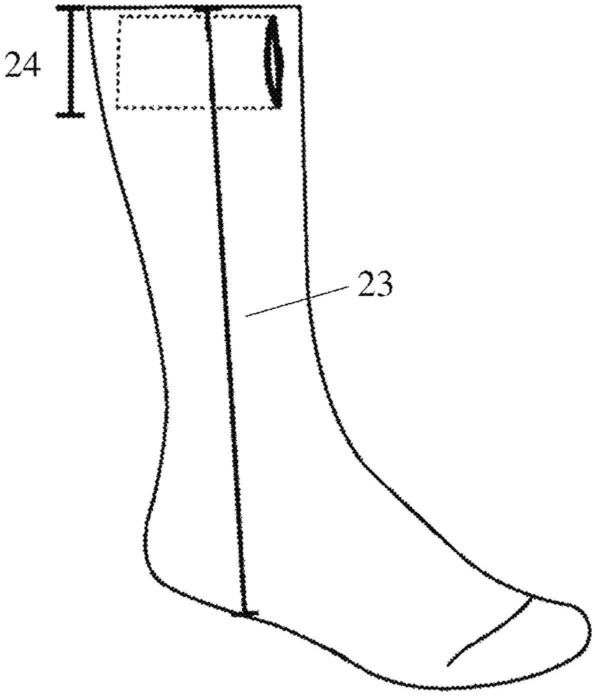
FIGS. 8A-B illustrate an exemplary embodiment of the stimulation device having (A) a foot covering portion and (B) a detachable material portion with a hook-and-loop fastening system.

Some exemplary measurement and placement of the two stimulation device components (i.e., foot covering and detachable material) are described herein. As shown in FIG. 8A, an exemplary foot covering is configured to fit the foot of the wearer having a foot length of 8½ inches and a foot width of 1¼ inches. In this representation, the foot covering is an ankle sock having a sock height 23 of 9 inches and a sock opening diameter of 3⅝ inches. The rib band cuff height 24 may be 2½ inches which may contain an electronic holding pouch having a width of 3 inches and a height of 2 inches. The pouch is to be placed in the center of the rib band cuff, preferably ½ inches from the center region.

Figure 8B:
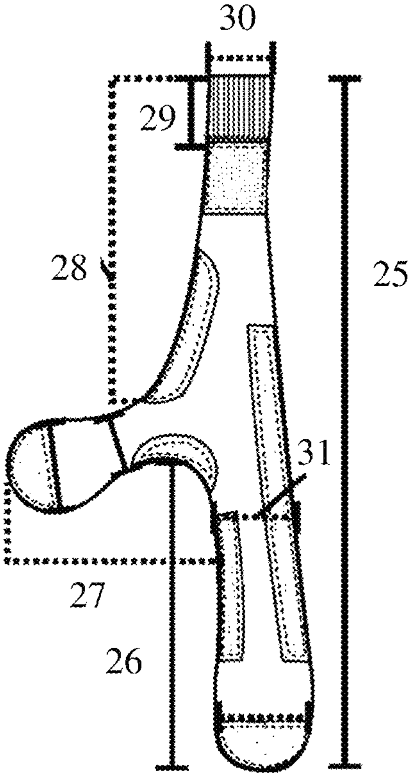

Referring to FIG. 8B, an exemplary detachable material for housing tactile actuators is shown. In this embodiment, the material has a total length 25 of 10 inches and a length of the longer finger 26 of about 4¼ inches with a width of 1½ inches 31. The length of the shorter finger 27 may be 2½ inches with a width of 1½ inches for the widest point and a 1¼ inches for the smallest point. In addition, the band/cuff region may have a height 29 of 1 inch and a width 30 of 1 inch. The length 28 from the opening of the foot covering to the start of the short finger may be 5 inches.

It is to be understood that this invention is not limited to any particular embodiment described herein and may vary. It is also to be understood that the terminology used herein is for the purpose of describing particular embodiments only, and is not intended to be limiting, since the scope of the present invention will be limited only by the appended claims.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

What is claimed is:

1. A wearable device configured for operation with tactile actuators which stimulate regions of a human foot, comprising:

a washable foot covering for use on a human foot having at least a foot top region and an ankle region, wherein the foot top region is alignable with a metatarsal region of the human foot when the washable foot covering is placed on the human foot, wherein the ankle region is alignable with at least one side of an ankle of the human foot when the foot cover is placed on the human foot;

an electronics holding pouch; and a material detachable from and securable to the washable foot covering, wherein the material creates at least a first placement region for a first tactile actuator at said foot top region of the washable foot covering and/or said ankle region of the washable foot covering, and wherein the material comprises one or more passageways for wires to extend from the electronics holding pouch to the at least a first placement region.

2. The device of claim 1 wherein the material creates at least a second placement region for a second tactile actuator in said foot top region of the washable foot covering or the ankle region of the washable foot covering, and wherein the at least a first placement region and the at least a second placement region are in different regions of the washable foot covering.

3. The device of claim 1 wherein the washable foot covering is configured as a sock.

4. The device of claim 3 wherein the sock is a crew sock.

5. The device of claim 3 wherein the sock is an ankle sock.

6. The device of claim 3 wherein in the sock is toeless.

7. The device of claim 1 wherein the washable foot covering is configured as a cuff.

8. The device of claim 1 wherein the material is secured to the washable foot covering by hook and loop connectors.

9. The device of claim 1 wherein the material is secured to the washable foot covering by an adhesive.

10. A stimulation device, comprising:

a washable foot covering for use on a human foot having at least a foot top region and an ankle region, wherein the foot top region is alignable with a metatarsal region of the human foot when the washable foot covering is placed on the human foot, wherein the ankle region is alignable with at least one side of an ankle of the human foot when the foot cover is placed on the human foot;

a first tactile actuator;

an electronic controller;

an electronics holding pouch configured to hold the electronic controller;

one or more wires which connect the electronic controller to the first tactile actuator; and a material detachable from and securable to the washable foot covering, wherein the material creates at least a first placement region for the first tactile actuator at said foot top region of the washable foot covering and/or said ankle region of the washable foot covering, wherein the material comprises one or more passageways for the one or more wires to extend from the electronics holding pouch to the at least a first placement region, wherein the electronic controller is connectable by the one or more wires to the first tactile actuator and the first tactile actuator is configured to provide vibratory stimulation to either the metatarsal region of the human foot or the plantar region of the human foot under the control of the electronic controller.

11. The stimulation device of claim 10 further comprising a second tactile actuator, and wherein the material creates at least a second placement region for the second tactile actuator in said foot top region of the washable foot covering or the ankle region of the washable foot covering, wherein the at least a first placement region and the at least a second placement region are in different regions of the washable foot covering, and wherein the material further comprises one or more further passageways for the one or more wires to extend from the electronics holding pouch region to the at least a second placement region, and wherein the electronic controller is connectable by the one or more wires to the second tactile actuator and the second tactile actuator is configured to provide vibratory stimulation to either the metatarsal region of the human foot or the plantar region of the human foot under the control of the electronic controller.

12. The stimulation device of claim 11 wherein the electronic controller controls the first tactile actuator and the second tactile actuator to provide vibratory stimulations that are different from each other.

13. The stimulation device of claim 10 further comprising a battery connected to the electronic controller, wherein the pouch region holds both the electronic controller and the battery.

14. The stimulation device of claim 10 wherein the washable foot covering is configured as a sock.

15. The stimulation device of claim 14 wherein the sock is a crew sock.

16. The stimulation device of claim 14 wherein the sock is an ankle sock.

17. The stimulation device of claim 14 wherein in the sock is toeless.

18. The stimulation device of claim 10 wherein the washable foot covering is configured as a cuff.

19. The stimulation device of claim 10 wherein the material is secured to the washable foot covering by hook and loop connectors.

20. The stimulation device of claim 10 wherein the material is secured to the washable foot covering by an adhesive.

* * * * *